(12) United States Patent
McLaughlin et al.

(10) Patent No.: US 8,332,009 B2
(45) Date of Patent: Dec. 11, 2012

(54) SENSORS

(75) Inventors: James Andrew McLaughlin, Belfast (GB); John McCune Anderson, Holywood (GB); Michael Skillen, Greystone (GB)

(73) Assignee: Intelesens Limited, Belfast (GB)

( * ) Notice: Subject to any disclaimer, the term of this patent is extended or adjusted under 35 U.S.C. 154(b) by 292 days.

(21) Appl. No.: 12/600,644

(22) PCT Filed: Apr. 30, 2008

(86) PCT No.: PCT/GB2008/001492
§ 371 (c)(1),
(2), (4) Date: Nov. 17, 2009

(87) PCT Pub. No.: WO2008/142365
PCT Pub. Date: Nov. 27, 2008

(65) Prior Publication Data
US 2010/0160762 A1 Jun. 24, 2010

(30) Foreign Application Priority Data

May 18, 2007 (GB) .................................. 0709531.8

(51) Int. Cl.
*A61B 5/0408* (2006.01)
*A61B 5/0416* (2006.01)
*A61B 5/11* (2006.01)
(52) U.S. Cl. ........ 600/372; 600/391; 600/393; 600/394; 600/595

(58) Field of Classification Search .................. 600/372, 600/393, 391, 394, 595
See application file for complete search history.

(56) References Cited

U.S. PATENT DOCUMENTS

| | | | | | |
|---|---|---|---|---|---|
| 4,067,342 | A | * | 1/1978 | Burton ........................... | 607/152 |
| 4,112,941 | A | * | 9/1978 | Larimore ...................... | 600/394 |
| 4,259,965 | A | * | 4/1981 | Fukuda et al. ................ | 600/392 |
| 4,270,543 | A | * | 6/1981 | Tabuchi et al. ................ | 600/396 |
| 4,653,503 | A | * | 3/1987 | Heath ........................... | 600/391 |
| 4,947,846 | A | * | 8/1990 | Kitagawa et al. ............. | 600/391 |
| 6,117,077 | A | * | 9/2000 | Del Mar et al. ............... | 600/301 |
| 6,912,414 | B2 | * | 6/2005 | Tong ............................. | 600/372 |
| 7,359,744 | B2 | * | 4/2008 | Lee et al. ...................... | 600/392 |
| 7,637,747 | B2 | * | 12/2009 | Jaatinen et al. ................ | 439/39 |
| 7,668,580 | B2 | * | 2/2010 | Shin et al. ..................... | 600/391 |

* cited by examiner

*Primary Examiner* — Lee S Cohen
(74) *Attorney, Agent, or Firm* — Foley and Lardner LLP; Christopher J. McKenna

(57) ABSTRACT

A two-part sensor (1) comprising a first part comprising a sensing device (3) which senses information, a second part comprising a receiving device (5) which receives a measure of the information, and a connector (7) comprising at least one first portion (21) which is magnetic and is attached to one of the sensing device and the receiving device, and at least one second portion (23) which is magnetizable and is attached to an other of the sensing device and the receiving device, wherein the first portion and the second portion are connectable and disconnectable to connect and disconnect the sensing device and the receiving device.

11 Claims, 1 Drawing Sheet

SENSORS

Figure 1:
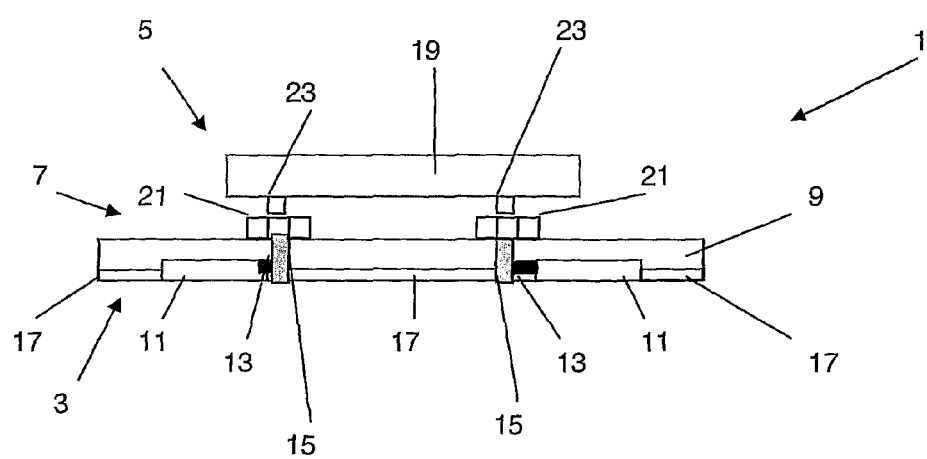

The invention relates to two-part sensors, and particularly, but not exclusively, to sensors for sensing electrical signals, for example ECG electrical signals or electrical signals produced as a result of blood flow through an artery.

A wide range of sensors exist, particularly for ECG measurement. One such sensor which is commonly used, comprises a plurality of electrodes for sensing ECG signals, a receiver for receiving the ECG signals, and a connector between each electrode and the receiver. The electrodes are typically attached to a plurality of locations of the chest of a user of the sensor. The receiver may be a unit located in the proximity of the user, or may be attached to a strap and worn around the waist of the user. The connectors are usually elongate to be able to reach between the electrodes and the receiver, and are flexible to be able to accommodate movement of the user. The connectors are connected to the electrodes by various types of connecting portions, including for example crocodile clips. It is important that good connection is achieved between the connectors and the electrodes, in order that the connection between the connectors and the electrodes is maintained, i.e. they cannot easily be inadvertently disconnected, and that good quality ECG signals may be measured. This is not always achieved with the sensors described above, and improvements in sensors are therefore desirable.

According to a first aspect of the invention there is provided a two-part sensor comprising
a first part comprising a sensing device which senses information,
a second part comprising a receiving device which receives a measure of the information, and
a connector comprising at least one first portion which is magnetic and is attached to one of the sensing device and the receiving device, and at least one second portion which is magnetisable and is attached to an other of the sensing device and the receiving device, wherein the first portion and the second portion are connectable and disconnectable to connect and disconnect the sensing device and the receiving device.

The connector first portion may be attached to the sensing device, and the connector second portion may be attached to the receiving device. Alternatively, the connector first portion may be attached to the receiving device, and the connector second portion may be attached to the sensing device.

The connector first portion and the connector second portion may be connectable by magnetic forces exerted by the first portion on the second portion. The connector second portion may be magnetisable by comprising a ferromagnetic material, for example high iron content steel. The connector second portion may be magnetic. The connector first portion and the connector second portion may be connectable by magnetic forces exerted by the first portion on the second portion and magnetic forces exerted by the second portion on the first portion. The magnetic forces may act to guide connection of the sensing device and the receiving device.

The connector first portion and the connector second portion may be connectable by magnetic forces which are configured more readily to release the receiving device from the sensing device than to release the sensing device from connection with a user of the sensor. The connector first portion and the connector second portion may be connectable by magnetic forces which are in a of range approximately 7 N to approximately 10 N. Thus a body-worn, two-part sensor is provided, the receiving device of which may be disconnected from the sensing device without disconnecting the sensing device from the body.

The connector first portion and the connector second portion may be disconnectable by force applied by a user of the sensor. The force may be in a range of approximately 7 N to approximately 10 N (equivalent to approximately a 700 g to approximately 1 kg weight pull or attraction).

The connector may comprise a plurality of connector first portions and a plurality of connector second portions, each connector first portion being connectable and disconnectable to a connector second portion. For example, the connector may comprise two connector first portions and two connector second portions. For example, the connector may comprise three connector first portions and three connector second portions. The connector first portions and the connector second portions may be attached to the sensing and receiving devices in a polarised arrangement, such as to dictate orientation of the receiving device with respect to the sensing device. For example, the connector may comprise three connector first portions and three connector second portions, attached to the sensing and receiving devices, typically but not exclusively, in a polarised arrangement comprising a triangular arrangement. In a preferred embodiment, the three connector first portions are attached to the sensing device in a triangular arrangement, and the three connector second portions are attached to the receiving device in a triangular arrangement. Using a polarised arrangement of the connector portions prevents misconnection of the sensing and receiving devices with respect to each other, and allows easy and rapid connection of the sensing and receiving devices, as a user does not have to determine how the devices should be oriented with respect to each other. A connector comprising three connector first portions and three connector second portions is particularly advantageous in that the connector provides secure connection and electrical safety, whilst the sensing and receiving devices may be more readily disconnected from each other than other connector portion arrangements, for example four connector first portions and four second portions arranged in a square.

The connector first portion and the connector second portion may transmit the measure of the information from the sensing device to the receiving device. For example, the measure of the information may comprise electrical signals, and the connector first portion and the connector second portion may transmit the electrical signals from the sensing device to the receiving device. The connector first portion and the connector second portion may form a low impedance path for the electrical signals. The connector first portion or the connector second portion may form a part of an electrode system of the sensor for electrical signal measurement. The connector first portion and the connector second portion may comprise chloride connector portions. Connectivity of the connector first portion and the connector second portion by magnetic forces achieves a good connection between the portions in terms of conductivity of electrical signals by the connector first portion and the connector second portion.

The connector first portion may comprise a female-type clip portion and the connector second portion may comprise a male-type stud portion, which portions mate with each other. Alternatively, the connector first portion may comprise a male-type stud portion and the connector second portion may comprise a female-type clip portion, which portions mate with each other.

The sensing device may sense information comprising movement. The movement may be caused, for example, by pulse wave velocity signals, for example, of blood in an artery of a user of the sensor. The sensing device may produce a measure of the movement information comprising electrical signals. The sensing device may comprise a material capable of sensing movement and producing electrical signals which are a measure of the movement.

The sensing device may sense information comprising electrical signals. The electrical signals may be caused, for example, by ECG signals of a user of the sensor, or respiration of a user of the sensor. The sensing device may produce a measure of the electrical signals.

The sensing device may comprise at least one electrode, capable of sensing information in the form of electrical signals and producing a measure of the electrical signals. The sensing device may comprise an array of electrodes, each capable of sensing information in the form of electrical signals and producing a measure of the electrical signals. The or each electrode may comprise a Ag/AgCl-hydrogel electrode. The or each electrode may be annulus shaped. The sensing device may comprise a polyester substrate, in which the or each electrode may be provided.

The sensing device may comprise a stud to connect the or each electrode to a connector first portion or a connector second portion attached to the sensing device. The or each stud may be magnetic. The or each stud may be provided with insulation in the form of a polyester substrate and a screen-printed dielectric ink. The or each electrode may be provided on a first surface of the sensing device, and the or each stud may form a through-hole connection to a connector first portion or a connector second portion attached to a second, opposite, surface of the sensing device. The sensing device may comprise a track to connect the or each electrode to the or each stud. The or each track may comprise silver and may be screen-printed in the sensing device. The or each track may be provided with insulation in the form of a polyester substrate and a screen-printed dielectric ink. For the or each electrode, the electrode may be provided on a first surface of the sensing device, a track may be provided on or near the first surface of the sensing device, in connection with the electrode, and a stud may be provided which forms a through-hole connection to a connector first portion or a connector second portion attached to a second, opposite, surface of the sensing device. The electrodes (and tracks when provided) may therefore be provided on or near a first surface of the sensing device, which is a surface attached adjacent to skin of a user of the sensor, and the connector first/second portion attached to an opposite side of the sensing device. Such an arrangement eases construction of the sensing device, and lowers consumable costs and the cost of manufacture of the sensing device.

The sensing device may comprise a patch provided with pressure-sensitive adhesive, for attachment of the sensing device to a user of the sensor. The patch may comprise an arrangement of spaced adhesive portions. The spacing is preferably optimised to ensure good attachment of the patch to the user.

The sensing device may be a disposable sensing device.

The receiving device may comprise a telemetry unit, for wireless sending of the measure of the information to an acquisition system. The receiving device may be a low-profile receiving device. This is particularly desirable when the sensor is to be worn by a user thereof. The receiving device may be a reusable receiving device.

Providing a two-part sensor in which the sensing device is a separate part from the receiving device, allows the relatively inexpensive sensing device to be disposable, whilst the relatively expensive receiving device is reusable.

Figure 2:
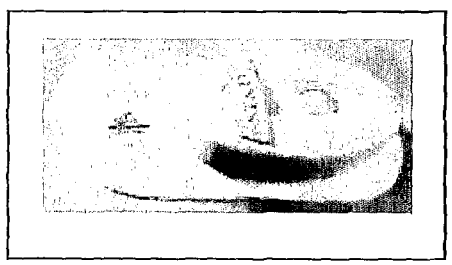
Figure 3:
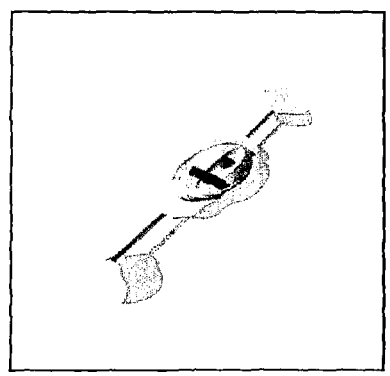

Embodiments of the present invention will now be described, by way of example only, with reference to the accompanying drawings in which:

FIG. 1 comprises a schematic cross sectional view of a two-part sensor according to a first embodiment of the invention;

FIG. 2 comprises a schematic representation of a two-part sensor according to a second embodiment of the invention, and FIG. 3 comprises a schematic representation of a two-part sensor according to a third embodiment of the invention.

FIG. 1 illustrates a two-part sensor 1 comprising a first part comprising a sensing device 3, a second part comprising a receiving device 5 and a connector 7. The sensor 1 is intended for use by a person, for sensing information in the form of electrical signals comprising ECG signals produced by the person's heart. The sensor thus monitors vital signs of the person. It will appreciated, however, that further embodiments of the invention may sense information other than electrical signals.

The sensing device 3 is in the form of a patch, and comprises a polyester substrate 9. Three electrodes 11 (only two of which are shown) are screen-printed, in a triangular arrangement, onto a first surface of the substrate 9, to protrude from the substrate 9, as shown. Each electrode comprises a Ag/AgCl-hydrogel electrode, in the shape of an annulus. The sensing device 3 further comprises a track 13 and a stud 15 for each electrode 11. The tracks 13 and the studs 15 are provided with insulation in the form of the polyester substrate and a screen-printed dielectric ink (not shown). Each track 13 comprises silver and is screen-printed onto the first surface of the substrate so as to be in connection with an electrode 11. Each stud 15 is magnetic, and has a first end which extends beyond the first surface of the substrate 9 and a second end at a second, opposite, surface of the substrate 9, i.e. each stud 15 forms a through-hole connection through the sensing device 3, as shown. The first end of each stud 15 is connected to a track 13, and the second end of each stud 15 is connected to the connector 7. The sensing device 3 further comprises an arrangement of spaced adhesive portions 17, comprising pressure-sensitive adhesive, provided on the first surface of the substrate 9, as shown.

The receiving device 5 comprises a telemetry unit 19. This receives the measure of the information from the sensing device, and wirelessly sends the measure of the information to an acquisition system (not shown). The receiving device 5 is designed to be low-profile.

The connector 7 comprises three connector first portions 21 (only two of which are shown), and three connector second portions 23 (only two of which are shown). The connector first portions 21 are attached to the sensing device 3 in a polarised, triangular arrangement, and the connector second portions 23 are attached to the receiving device 5 in a polarised, triangular arrangement. The triangular arrangement of the connector first portions 21 corresponds to the triangular arrangement of the electrodes 11, tracks 13 and studs 15 of the sensing device 3, and each connector first portion 21 is attached to a stud 15. The triangular arrangement of the connector first portions 21 also substantially corresponds to the triangular arrangement of the connector second portions 23. The connector first portions 21 each comprise a female-type clip portion and the connector second portions 23 each comprise a male-type stud portion, which portions mate with each other. The connector first portions 21 are each magnetic, and the connector second portions 23 are each magnetisable by comprising high iron content steel. Each pair of a connector first portion 21 and a connector second portion 23 is connectable by magnetic forces exerted by the first portion on the second portion. The magnetic forces are configured more readily to release the receiving device 5 from the sensing device 3 than to release the sensing device 3 from connection with the body of the person using the sensor 1, and are in a of range approximately 7 N to approximately 10 N. Each pair of a connector first portion 21 and a connector second portion 23 transmits the measure of the information (comprising electrical signals) from the sensing device 3 to the receiving device 5, and form a low impedance path for the electrical signals.

In use, the two-part sensor 1 is positioned on the body of the person using the sensor 1. In this embodiment, the sensing device 3 is attached to the skin of the chest of the person, using the adhesive portions 17 of the sensing device 3. The first surface of the substrate 9 of the sensing device 3 is then positioned adjacent the person, and the second, opposite, surface of the substrate 9 faces away from the person. Once the sensing device 3 has been securely attached to the person, the receiving device 5 is connected to the sensing device 3, using the connector 7. Each connector second portion 23, connected to the receiving device 5, is brought into proximity with a connector first portion 21, connected to the sensing device 3. The magnetic forces between the connector first and second portions act to guide connection of the portions, such that each male-type stud of a connector second portion 23 mates with a female-type clip of a connector first portion 21. As the three connector first portions 21 are attached to the sensing device 3 in a polarised, triangular arrangement, and the three connector second portions 23 are attached to the receiving device 5 in a polarised, triangular arrangement, the orientation of the receiving device 5 with respect to the sensing device 3 is easily determined. Such an arrangement of the connector first and second portions prevents misconnection of the sensing and receiving devices with respect to each other. The coupling between each pair of a connector first portion 21 and a connector second portion 23 is strong enough to hold the receiving device 5 to the sensing device 3 (preventing inadvertent disconnection), but weak enough to allow disconnection of the devices without detaching the sensing device 3 from the body of the person. The sensing and receiving devices are disconnectable by force applied by the person using the sensor 1. The force should be in the range of approximately 7 N to approximately 10 N (equivalent to approximately 700 g to approximately 1 kg weight). The sensing device 3 and the receiving device 5 may thus be connectable to each other and disconnectable from each other, with ease. This is particularly advantageous as the sensing device 3 will generally be a relatively cheap item, and therefore can be disposable, whereas the receiving device 5 will generally be a relatively expensive item, and therefore will desirable be reusable.

In this embodiment, each electrode 11 of the sensing device 3 senses information in the form of electrical signals comprising ECG signals produced by the heart of the person using the sensor 1. Each electrode 11 produces a measure of the electrical signals, which comprises the electrical signals, and transmits the signals to a track 13 connected to the electrode 11. Each track 13 transmits the electrical signals to a stud 15 attached to the track 13. Each stud 15 transmits the electrical signals to a connector first portion 21 attached thereto. Each connector first portion 21 transmits the electrical signals to a connector second portion 23 connected thereto. The electrical signals are thus transmitted from the sensing device 3 to the receiving device 5, which may then transmit the signals to an acquisition unit.

FIG. 2 illustrates a schematic representation of a second embodiment of a two-part sensor of the invention. The sensor comprises a sensing device in the form of a patch, as shown, and a receiving device connected to the sensing device by a connector, as shown. The sensing device senses information comprising electrical signals, caused by ECG signals of a user of the sensor, or respiration of a user of the sensor.

FIG. 3 illustrates a schematic representation of a third embodiment of a two-part sensor of the invention. The sensor comprises a sensing device in the form of a patch, as shown, a receiving device connected to the sensing device by a connector, as shown, and two further patches attached to the sensor. The sensing device of this embodiment senses information comprising movement, caused, for example, by pulse wave velocity signals of blood in an artery of a user of the sensor. The sensing device produces a measure of the movement information comprising electrical signals, and comprises a material capable of sensing movement and producing electrical signals which are a measure of the movement.

The two-part sensors of the invention provide the ability to have a disposable sensing device and a reusable receiving device, are easy to use as the receiving device may be readily connected to the sensing device using the polarised connection arrangement, and may be disconnected from the sensing device without disconnecting the sensing device from the user, are comfortable to use due to the low profile of the receiving device, provide good electrical signal acquisition due to the use of a magnetic connector, and have low construction costs due to the arrangement of the electrodes and connector on opposite sides of the sensing device.

What is claimed:

1. A two-part sensor comprising a first part comprising a sensing device which senses information, a second part comprising a receiving device which receives a measure of the information, and a connector comprising at least one first portion which is magnetic and is attached to one of the sensing device and the receiving device, and at least one second portion which is magnetic and is attached to an other of the sensing device and the receiving device, wherein the first portion and the second portion are connectable and disconnectable to connect and disconnect the sensing device and the receiving device; and in which the connector first portion and the connector second portion are connectable by magnetic forces exerted by the first portion on the second portion and magnetic forces exerted by the second portion on the first portion and in which the magnetic forces are configured more readily to release the receiving device from the sensing device than to release the sensing device from connection with a user of the sensor;

in which the connector further comprises a plurality of connector first portions and a plurality of connector second portions, each connector first portion being connectable and disconnectable to a connector second portion; and in which the connector first portions and the connector second portions are attached to the sensing and receiving devices in a polarised arrangement, such as to dictate orientation of the receiving device with respect to the sensing device.

2. A two-part sensor according to claim 1, in which the connector first portion and the connector second portion are connectable by magnetic forces which are in a range of approximately 7 N to approximately 10 N.

3. A two-part sensor according to claim 1, in which the connector comprises three connector first portions and three connector second portions, attached to the sensing and receiving devices in a polarised arrangement comprising a triangular arrangement.

4. A two-part sensor according to claim 1, in which the connector first portion and the connector second portion transmit the measure of the information from the sensing device to the receiving device.

5. A two-part sensor according to claim 1, which senses information comprising movement.

6. A two-part sensor according to claim 1, which senses information comprising electrical signals.

7. A two-part sensor according to claim 1, in which the sensing device comprises at least one electrode, capable of sensing information in the form of electrical signals and producing a measure of the electrical signals.

8. A two-part sensor according to claim 6, in which the sensing device comprises a stud to connect the or each electrode to a connector first portion or a connector second portion attached to the sensing device.

9. A two-part sensor according to claim 7, in which the or each electrode is provided on a first surface of the sensing device, and the or each stud forms a throughhole connection to a connector first portion or a connector second portion attached to a second, opposite, surface of the sensing device.

10. A two-part sensor according to claim 7, in which the sensing device comprises a track to connect the or each electrode to the or each stud.

11. A two-part sensor according to claim 1, in which the sensing device is a disposable sensing device, and the receiving device is a reusable receiving device.

* * * * *